United States Patent [19]

Angelo et al.

[11] Patent Number: 5,047,568
[45] Date of Patent: Sep. 10, 1991

[54] SULFONIUM SALTS AND USE AND PREPARATION THEREOF

[75] Inventors: Raymond W. Angelo, Endwell; Jeffrey D. Gelorme, Binghamton; Joseph P. Kuczynski, Apalachin; William H. Lawrence, Greene, all of N.Y.; Socrates P. Pappas, Fargo, N. Dak.; Logan L. Simpson, Austin, Tex.

[73] Assignee: International Business Machines Corporation, Armonk, N.Y.

[21] Appl. No.: 272,965

[22] Filed: Nov. 18, 1988

[51] Int. Cl.$^5$ .................. C07C 381/12; C08G 59/68; C08G 59/72
[52] U.S. Cl. ........................................ 556/64; 522/31; 522/170; 430/280; 430/914; 562/113; 568/6; 568/13; 568/18
[58] Field of Search ................. 556/64; 568/6, 13, 18; 562/113

[56] References Cited

U.S. PATENT DOCUMENTS

| 3,190,893 | 6/1965 | Holm | 260/351 |
| 3,484,467 | 12/1969 | Susi et al. | 260/440 |
| 3,969,414 | 7/1976 | Frenier et al. | 549/78 |
| 3,981,897 | 9/1976 | Crivello | 260/440 |
| 4,058,401 | 11/1977 | Crivello | 96/115 R |
| 4,069,054 | 1/1978 | Smith | 96/115 P |
| 4,069,055 | 1/1978 | Crivello | 96/115 R |
| 4,081,276 | 3/1978 | Crivello | 96/35.1 |
| 4,136,102 | 1/1979 | Crivello | 260/440 |
| 4,161,478 | 7/1979 | Crivello | 260/327 B |
| 4,250,053 | 2/1981 | Smith | 252/426 |
| 4,256,828 | 3/1981 | Smith | 430/280 |
| 4,310,469 | 1/1982 | Crivello | 260/446 |
| 4,442,197 | 4/1984 | Crivello et al. | 430/280 |
| 4,503,211 | 3/1985 | Robins | 528/92 |
| 4,537,725 | 8/1985 | Irving | 556/138 |
| 4,684,671 | 8/1987 | Tsuchiya et al. | 522/31 |
| 4,708,925 | 11/1987 | Newman | 430/270 |
| 4,760,013 | 7/1988 | Haeker et al. | 522/31 |
| 4,791,213 | 12/1988 | Gawne et al. | 522/31 |
| 4,837,124 | 6/1989 | Wu et al. | 522/31 |
| 4,933,377 | 6/1990 | Saeva | 522/31 |

FOREIGN PATENT DOCUMENTS

| 0142384 | 5/1985 | European Pat. Off. |
| 331496 | 9/1989 | European Pat. Off. ............. 556/64 |
| 2269551 | 11/1975 | France . |
| WO80/01695 | 8/1980 | PCT Int'l Appl. . |

OTHER PUBLICATIONS

Crivello et al., "Complex Triarylsulfonium Salt Photoinitiators, II, The Preparation of Several New Complex Triarylsulfonium Salts and the Influence of Their Structure in Photoinitiated Cationic Polymerization," Journal of Polymer Science: Polymer Chemistry Edition, vol. 18, 2697-2714, 1980, John Wiley & Sons.
Crivello et al., "New Photoinitiators For Cationic Polymerization," Journal of Polmer Science: Symposium No. 56, pp. 383-395, 1976, John Wiley & Sons, Inc.
Watt et al., "A Novel Photoiniator of Cationic Polymerization: Preparation and Characterization of Bis[-4-(Diphenylsulfonio)Phenyl]Sulfide-Bis-Hexafluorophosphate," Journal of Polymer Science: Polymer Chemistry Edition, vol. 22, 1797-1801, 1984.
Papas et al., "Photoinitiation of Cationic Polymerizatiion, III, Photosensitization of Diphenyliodonium and Triphenylsulfonium Salts," Journal of Polymer Science: Polymer Chemistry Edition, vol. 22, 77-84 (1984).
Crivello et al., "Photoinitiated Cationic Polymerization With Triarylsulfonium Salts," Journal of Polymer Science: Polymer Chemistry Edition, vol. 17, 977-999, (1979).
Crivello et al., "Complex Triarylsulfonium Salt Photoinitiators, I, The Identification, Characterization, and Syntheses of A New Class of Triarylsulfonium Salt Photoinitiators," Journal of Polymer Science: Polymer Chemistry Edition, vol. 18, 2677-2695, 1980.
Crivello, "Cationic Polymerization-Iodonium and Sulfonium Salt Photoiniators," General Electric Corporate Research and Development Center, Schenectady, NY.
Daub et al., "The Monocyanoethylation of Anthrone, An Improved Synthesis of $\beta$-(9,10-Dihydro-9-Anthranyl)-Propionic Acid," Laboratory of Organic Chemistry, vol. 74, pp 4449-4450, Sep. 5, 1952.
Ito, "Novel Polymeric Dissolution Inhibitor . . . ", J. Electrochem. Soc., vol. 135, No. 9, pp. 2328-2333.
Ito, "Evaluation of Onium Salt . . . ", J. Electrochem. Soc.: Solid State Science and Technology, vol. 135, No. 9, pp. 2322-2327.
Arnold et al., "Homolytic Versus Heterolytic Cleavage . . . ", vol. 63, No. 11, Nov. 1985, pp. 3140-3146, Can. J. Chem.

Primary Examiner—Marion E. McCamish
Assistant Examiner—Arthur H. Roeckert
Attorney, Agent, or Firm—Pollock, Vande Sande & Priddy

[57] ABSTRACT

Sulfonium salts of the formula:

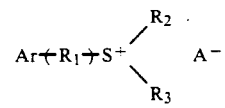

wherein Ar is a fused aromatic radical; $R_1$ is a divalent organic bridge; each $R_2$ and $R_3$ individually is an alkyl, aryl, alkaryl, aralkyl or substituted aryl, provided thatn not more than one of $R_2$ and $R_3$ is alkyl; and A is a non-nucleophilic anion; use thereof and preparation thereof.

12 Claims, No Drawings

SULFONIUM SALTS AND USE AND PREPARATION THEREOF

DESCRIPTION

1. Technical Field

The present invention is concerned with new sulfonium salts and especially with such salts that are useful as photoinitiators.

In addition, the present invention is concerned with the preparation of such compounds and their use as photoinitiators, especially in cationic polymerizations.

2. Background Art

Various compounds have been suggested as photoinitiators for photochemically induced cationic polymerizations of such materials as epoxy resins, cyclic ethers, cyclic esters, polyvinyl acetals, phenoplasts, and aminoplasts.

Along these lines, see U.S. Pat. No. 4,161,478 to Crivello, and Watt, et al., "A Novel Photoinitiator of Cationic Polymerization: Preparation and Characterization of Bis[4-(diphenylsulfonio)phenyl]- sulfide-Bis-Hexafluorophosphate", *Journal of Polymer Science: Polymer Chemistry Edition*, Vol. 22, p. 1789, 1980 John Wiley & Sons, Inc. Certain sulfonium and iodonium salts have been suggested as the initiators for such cationic polymerizations. Additional discussions concerning these previously suggested sulfonium and iodonium salts can be found, for instance, in Pappas, et al., "Photoinitiation of Cationic Polymerization. III. Photosensitization of Diphenyliodonium and Triphenylsulfonium Salts", *Journal of Polymer Science: Polymer Chemistry Edition*, Vol. 22, pp. 77-84, 1984 John Wiley & Sons, Inc.; Crivello, et al., "Photoinitiated Cationic Polymerization with Triarylsulfonium Salts", *Journal of Polymer Science: Polymer Chemistry Edition*, Vol. 17, pp. 977-999, 1979 John Wiley & Sons, Inc.; Crivello, et al., "Complex Triarylsulfonium Salt Photoinitiators. I. The Identification, Characterization, and Syntheses of a New Class of Triarylsulfonium Salt Photoinitiators", *Journal of Polymer Science: Polymer Chemistry Edition*, Vol. 18, pp. 2677-2695, 1980 John Wiley & Sons, Inc.; and Crivello, "Cationic Polymerization - Iodonium and Sulfonium Salt Photoinitiators", *Advances in Polymer Science*, Series #62, pp. 1-48.

However, the various sulfonium and iodonium salts suggested have not been entirely satisfactory since such salts exhibit relatively poor absorptivity, which thereby limits their use to employing near ultraviolet exposures. This problem is especially pronounced when the compositions to be polymerized are to be used for various photoresist applications since the bulk of the exposure of such applications is usually conducted employing mercury arc lamps. Accordingly, this spectral mismatch between the absorptivity of the photoinitiator and the output from the mercury arc lamp necessitates rather lengthy and costly exposure dosages.

SUMMARY OF THE INVENTION

In accordance with the present invention, new sulfonium compounds are provided that are useful as photoinitiators and that dramatically reduce the exposure requirement for photochemically induced cationic polymerization.

The compounds of the present invention exhibit increased absorption at the major mercury arc lamp lines as compared to the prior art sulfonium and iodonium photoinitiators. In addition, compounds of the present invention have significantly higher melting points as compared to prior art photoinitiators. This, in turn, results in increased thermal stability and shelf-life of compositions employing these compounds.

In particular, the present invention is concerned with compounds represented by the following formula:

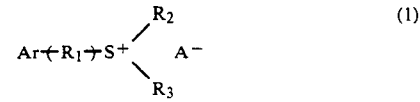

In the above formula, Ar is anthracyl, naphthyl, peryl, or pyryl. $R_1$ is an alkylene or alkenylene group that can be broken with an oxygen atom along the chain and/or can be substituted with a pendent hydroxyl group. Each $R_2$ and $R_3$, individually, is an aryl group, substituted aryl, alkyl group, alkaryl group, or aralkyl provided that not more than one of $R_2$ and $R_3$ is an alkyl group. $A^-$ is a non-nucleophilic anion such as $SbF_6$, $PF_6$, $AsF_6$, $BF_4$, $CF_3SO_3$, or $ClO_4$.

Those compounds of the present invention wherein $R_1$ is a substituted alkylene or alkenylene group having pendent hydroxyl groups are reactive with various of the polymers being polymerized such as the epoxy polymers and thereby become covalently bonded into the resin network. This is especially desirable when the photocured epoxy resins are to be subsequently employed in products such as circuit boards that involve plating copper thereon.

For instance, sulfur and sulfur-containing compounds are typical materials that tend to poison electroless copper plating baths which thereby effect the plating rate and quality of the plated copper. Accordingly, leaching out of sulfonium salts from the cured polymer of, for instance, a permanent photoresist into the additive plating bath is believed to cause deterioration of the plated copper quality.

Accordingly, with respect to those compounds of the present invention that are covalently bonded into the epoxy resin, the ability to be leached out of the resin is significantly reduced, if not entirely eliminated. In turn, the use of such sulfonium compounds will not adversely effect any plated copper.

In addition, the present invention is concerned with photocurable compositions that contain an epoxy polymer and at least one of the above-defined compounds. Such compounds are present in an amount sufficient to accelerate the cure of the epoxy polymer.

A further aspect of the present invention is concerned with a process for preparing a compound of Formula 1 wherein the $R_1$ group is a hydroxyl derivative. The process comprises reacting a compound of the formula Ar-$R_4$, wherein $R_4$ is a glycidyl ether group with a compound of the formula $R_2SR_3$, wherein $R_2$ and $R_3$ have the same meanings as discussed above. The reaction is carried out in the presence of hydrogen ions and a non-nucleophilic anion such as one or more of the following ions: $SbF_6$, $PF_6$, $AsF_6$, $BF_4$, $CF_3SO_3$, and $ClO_4$. The reaction is carried out in an organic diluent.

In addition, the present invention is concerned with a process for preparing those compounds of Formula 1 above that includes reacting a compound of the formula Ar-$R_1$X, wherein X is a halide and $R_1$ has the same meaning defined above, a compound of the formula $R_2SR_3$, wherein $R_2$ and $R_3$ have the same meanings as defined above, with a metallic compound of the anion such as a compound of the group MSbF$_6$, MPF$_6$, MAsF$_6$, MBF$_4$, CF$_3$SO$_3$M, MClO$_4$, or dioxane adducts thereof. The reaction is carried out in an organic diluent.

BEST AND VARIOUS MODES FOR CARRYING OUT THE INVENTION

The present invention is concerned with new sulfonium compounds that are especially useful as photoinitiators. The compounds of the present invention are represented by the following formula:

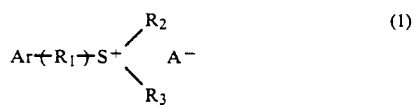

Ar of the above fused aromatic radical that is selected from the group of naphthyl, anthracyl, peryl, and pyryl. R$_1$ is a divalent bridge selected from the group of alkylene and alkenylene, alkylene and alkenylene chains broken with an oxygen atom; and substituted derivatives of the above chains. The substituted derivatives are those having pendent from the chain a hydroxyl group. R$_1$ usually contains about 1-10 carbon atoms and preferably about 1-4 carbon atoms.

Examples of specific R$_1$ bridges include methylene, ethylene, propylene, isopropylidene, butylene, isobutylene, oxymethylene, oxypropylene, and 3-hydroxy-1-oxybutylene.

Each R$_2$ and R$_3$ is individually an alkyl, aryl, substituted aryl, alkaryl, or aralkyl group, provided that not more than one of R$_2$ and R$_3$ is an alkyl group. Generally, the alkyl groups contain 1-12 carbon atoms and preferably 1-4 carbon atoms, examples of which are methyl, ethyl, propyl, isopropyl, and butyl. The aryl groups can contain 6-12 carbon atoms and include phenyl, biphenyl, and naphthyl. The substituted aryl groups are generally those substituted with one of the groups of OH, OR', NH$_2$, NR'R" wherein each R' and R" is individually an alkyl group containing generally 1-4 carbon atoms, including methyl and ethyl. The alkaryl groups generally contain about 1-18 carbon atoms and preferably about 7-10 carbon atoms and include phenyl, and ethylbenzyl. The aralkyl groups usually contain from about 7-18 carbon atoms and preferably from about 7-10 carbon atoms and include tolyl and xylyl.

A$^-$, in the above formula is a non-nucleophilic anion which can be SbF$_6$, PF$_6$, AsF$_6$, BF$_4$, CF$_3$SO$_3$, or ClO$_4$.

The compounds of the present invention can be used as photoinitiators for cationic polymerizations such as polymerizations of epoxy polymer, phenoplast, aminoplast, polyvinylacetals, cyclic ethers, and cyclic esters.

Typical examples of epoxy polymers include the epoxidized novolak polymers and the polyepoxides from halo-epoxy alkanes such as epichlorohydrin and a polynuclear dihydric phenol such as bisphenol A. Mixtures of epoxides can be used when desired.

The epoxidized novolak polymers are commercially available and can be prepared by known methods by the reaction of a thermoplastic phenolic aldehyde of a phenol with a halo-epoxy alkane. The phenol can be a mononuclear or polynuclear phenol. Examples of mononuclear phenols have the formula:

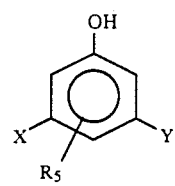

wherein X, Y, and R$_5$ are hydrocarbons containing no more than about 12 carbon atoms.

Hydrocarbon-substituted phenols having two available positions ortho or para to a phenolic hydroxy group for aldehyde condensation to provide polymers suitable for the preparation of epoxy novolaks include o- and p-cresols, o- and p-ethyl phenols, o- and p-isopropyl phenols, o- and p-tert-butyl phenols, o- and p-secbutyl phenols, o- and p-amyl phenols, o- and p-octyl phenols, o- and p-nonyl phenols, 2,5-xylenol, 3,4-xylenol, 2,5-diethyl phenol, 3,4-diethyl xylenol, 2,5-diisopropyl phenol, 4-methyl resorcinol, 4-ethyl resorcinol, 4-isopropyl resorcinol, 4-tert-butyl resorcinol, o- and p-benzyl phenol, o- and p-phenethyl phenols, o- and p-phenyl phenols, o- and p-tolyl phenols, o- and p-xylyl phenols, o- and p-cyclohexyl phenols, o- and p-cyclopentyl phenols, 4-phenethyl resorcinol, 4-tolyl resorcinol, and 4-cyclohexyl resorcinol.

Various chloro-substituted phenols which can also be used in the preparation of phenol-aldehyde resins suitable for the preparation of the epoxy novolaks include o- and p-chloro-phenols, 2,5-dichloro-phenol, 2,3-dichloro-phenol, 3,4-dichloro-phenol, 2-chloro-3-methyl-phenol 2-chloro-5-methyl-phenol, 3-chloro-2-methyl-phenol, 5-chloro-2-methyl-phenol, 3-chloro-4-methyl-phenol, 4-chloro-3-methyl-phenol, 4-chloro-3-ethyl-phenol, 4-chloro-3-isopropyl-phenol, 3-chloro-4-phenyl-phenol, 3-chloro-4-chloro-phenyl-phenol, 3,5-dichloro-4-methyl-phenol, 3,5-dichloro-5-methyl-phenol, 3,5-dichloro-2-methyl-phenol, 2,3-dichloro-5-methylphenol, 2,5-dichloro-3-methyl-phenol, 3-chloro-4,5-dimethyl-phenol, 4-chloro-3,4-dimethyl-phenol, 2-chloro-3,5-dimethyl-phenol, 5-chloro-2,3-dimethyl-phenol, 5-chloro-3,5-dimethyl-phenol, 2,3,5-trichloro-phenol, 3,4,5-trichloro-phenol, 4-chloro-resorcinol, 4,5-dichloro-resorcinol, 4-chloro-5-methyl-resoroinol, 5-chloro-4-methyl-resorcinol.

Typical phenols which have more than two positions ortho or para to a phenolic hydroxy group available for aldehyde condensation and which, by controlled aldehyde condensation, can also be used are: phenol, m-cresol, 3,5-xylenol, m-ethyl and m-isopropyl phenols, m,m'-diethyl and diisopropyl phenols, m-butyl-phenols, m-amyl phenols, m-octyl phenols, m-nonyl phenols, resorcinol, 5-methyl-resorcinol, 5-ethyl resorcinol.

Examples of polynuclear dihydric phenols are those having the formula:

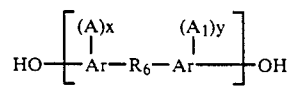

wherein Ar is an aromatic divalent hydrocarbon such as naphthylene and, preferably, phenylene; A and A$_1$ which can be the same or different are alkyl radicals, preferably having from 1 to 4 carbon atoms, halogen atoms, i.e., fluorine, chlorine, bromine, and iodine, or alkoxy radicals, preferably having from 1 to 4 carbon atoms; x and y are integers having a value 0 to a maximum value corresponding to the number of hydrogen atoms on the aromatic radical (Ar) which can be replaced by substituents and $R_6$ is a bond between adjacent carbon atoms as in dihydroxydiphenyl or is a divalent radical including, for example:

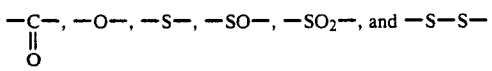

and divalent hydrocarbon radicals, such as-alkylene, alkylidene, cycloaliphatic, e.g., cycloalkylene and cycloalkylidene, halogenated, alkoxy or aryloxy substituted alkylene, alkylidene and cycloaliphatic radicals, as well as alkarylene and aromatic radicals including halogenated, alkyl, alkoxy or aryloxy substituted aromatic radicals and a ring fused to an Ar group; or $R^1$ can be polyalkoxy, or polysiloxy, or two or more alkylidene radicals separated by an aromatic ring, a tertiary amino group, an ether linkage, a carbonyl group or a sulfur containing group such as sulfoxide, and the like.

Examples of specific dihydric polynuclear phenols include, among others, the bis-(hydroxyphenyl)alkanes such as 2,2'-bis-(4-hydroxyphenyl)propane, 2,4'-dihydroxydiphenylmethane, bis-(2-hydroxyphenyl)methane, bis(4-hydroxyphenyl)methane, bis(4-hydroxy-2,6-dimethyl-3-methoxyphenyl)methane, 1,1'-bis-(4-hydroxyphenyl)ethane, 1,2'-bis-(4-hydroxyphenyl)ethane, 1,1'-bis-(4-hydroxy-2-chlorphenyl)ethane, 1,1'-bis(3-methyl-4-hydroxyphenyl) ethane, 1,3'-bis-(3-methyl-4-hydroxyphenyl)propane, 2,2'-bis-(3-phenyl-4-hydroxyphenyl)propane, 2,2'-bis-(3- isopropyl-4-hydroxyphenyl)propane, 2,2'-bis(2-isopropyl-4-hydroxyphenyl)pentane, 2,2'-bis-(4-hydroxyphenyl) heptane, bis-(4-hydroxyphenyl)phenylmethane, bis-(4-hydroxyphenyl)cyclohexylmethane, 1,2'-bis-(4-hydroxy- phenyl)-1,2'-bis-(phenyl)propane and 2,2'-bis-(4- hydroxyphenyl)-1-phenyl-propane; di(hydroxyphenyl) sulfones such as bis-(4-hydroxyphenyl)sulfone, 2,4'-dihydroxydiphenylsulfone, 5'-chloro-2,4'-dihydroxydiphenyl sulfone, and 5'-chloro-4,4'-dihydroxydiphenyl sulfone; di(hydroxyphenyl)ethers such as bis-(4-hydroxyphenyl)ether, the 4,4'-, 4,2'-, 2,2'-, 2,3'-, dihydroxydiphenyl ethers, 4,4'-dihydroxy-2,6-dimethyldiphenyl ether, bis-(4-hydroxy-3-isobutylphenyl)ether, bis-(4-hydroxy-3-isopropylphenyl)ether, bis-(4-hydroxy-3-chlorophenyl)ether, bis-(4-hydroxy-3-fluorophenyl) ether, bis-(4-hydroxy-3-bromophenyl)ether, bis-(4-hydroxynaphthyl)ether, bis-(4-hydroxy-3-chloronaphthyl) ether, bis-(2-hydroxydiphenyl)ether, 4,4'-dihydroxy-2,6-dimethoxydiphenyl ether, and 4,4'-dihydroxy-2,5-diethoxydiphenyl ether.

The preferred dihydric polynuclear phenols are represented by the formula:

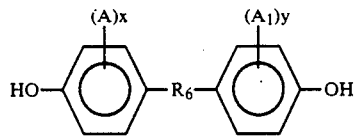

wherein A and $A_1$ are as previously defined, x and y have values from 0 to 4 inclusive and $R_6$ is a divalent saturated aliphatic hydrocarbon radical, particularly alkylene and alkylidene radicals having from 1 to 3 carbon atoms, and cycloalkylene radicals having up to and including 10 carbon atoms. The most preferred dihydric phenol is bisphenol A, i.e., 2,2'-bis(p-hydroxyphenyl)propane.

As condensing agents, any aldehyde may be used which will condense with the particular phenol being used, including formaldehyde. acetaldehyde, propionaldehyde, butyraldehyde, heptaldehyde,, cyclohexanone, methyl cyclohexanone, cyclopentanone, benzaldehyde, and nuclear alkyl-substituted benzaldehydes, such as toluic aldehyde, naphthaldehyde, furfuraldehyde, glyoxal, acrolein, or compounds capable of engendering aldehydes such as para-formaldehyde, hexamethylene tetramine. The aldehydes can also be used in the form of a solution, such as the commercially available formalin. The preferred aldehyde is formaldehyde.

The halo-epoxy alkane can be represented by the formula:

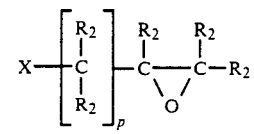

wherein X is a halogen atom (e.g., chlorine, bromine, and the like), p is an integer from 1-8, each $R_2$ individually is hydrogen or alkyl group of up to 7 carbon atoms; wherein the number of carbon atoms in any epoxy alkyl group totals no more than 10 carbon atoms.

While glycidyl ethers, such as derived from epichlorohydrin, are particularly preferred in the practice of this invention, the epoxy polymers containing epoxyalkoxy groups of a greater number of carbon atoms are also suitable. These are prepared by substituting for epichlorohydrin such representative corresponding chlorides or bromides of monohydroxy epoxyalkanes as 1- chloro-2,3-epoxybutane, 1-chloro-3,4-epoxybutane, 2- chloro-3,4-epoxybutane, 1-chloro-2-methyl-2,3-epoxypropane, 1-bromo-2,3-epoxypentane, 2-chloromethyl-1,2-epoxybutane, 1-bromo-4-methyl-3,4-epoxypentane, 1-bromo-4-ethyl-2,3-epoxypentane, 4-chloro-2-methyl-2,3-epoxypentane, 1-chloro-2,3-epoxyoctane, 1-chloro-2- methyl-2,3-epoxyoctane, or 1-chloro-2,3-epoxydecane. Although it is possible to use haloepoxyalkanes having a greater number of carbon atoms than indicated above, there is generally no advantage in using those having a total of more than 10 carbon atoms.

The preferred epoxidized novolak employed in the present invention is represented by the average formula:

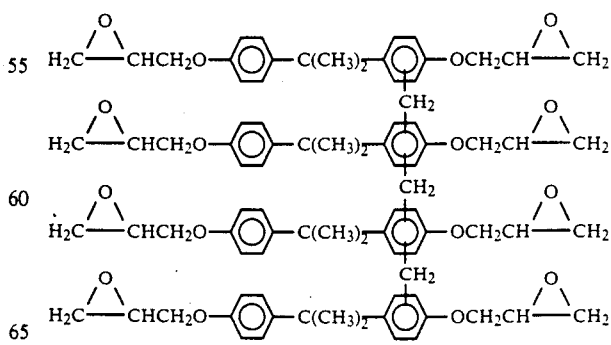

Such is commercially available under the trade designation EPI-REZ SU8.

In addition, the polyepoxides of halo epoxy alkane of the type discussed above and a polynuclear dihydric phenol of the type above can be employed. The preferred polyepoxides of this class being the polyepoxides of epichlorohydrin and bisphenol A, i.e., 2,2-bis(p-hydroxyphenyl)propane.

The compounds of the present invention, when used as photoinitiators, are generally employed in amounts of up to about 10% by weight based upon the material being polymerized and generally from about 0.5% to about 4% by weight.

Compounds of the present invention can be obtained by reacting a compound of the formula $Ar-R_1X$ wherein X is a halide and preferably bromine and Ar and $R_1$ are the same as defined above; with a compound of the formula $R_2SR_3$ wherein $R_2$ and $R_3$ are the same as defined above; along with a metallic compound of the non-nucleophilic anion such as a compound selected from the group of $MSbF_6$, $MPF_6$, $MAsF_6$, $MBF_4$, $CF_3SO_3M$, $MClO_4$, and dioxane adducts thereof. M is a monovalent alkali or transition metal and preferably is silver. The reaction is carried out in an organic diluent such as dichloromethane, chloroform, and tetrahydrofuran.

Approximately stoichiometric amounts of the above reactants are employed. An excess amount of diluent is used to ensure dissolution of the reactants.

When a dioxane adduct of the silver compound is employed, such can be obtained by the procedure suggested by Woodhouse, et al., *Journal of the American Chemical Society*, 14 (21), page 5586, 1982.

The reaction mass is permitted to stand at about room temperature for several days, such as from about 5-14 days, typical of which is about 10 days, to provide the desired product in the desired yield. The product can be separated from the reaction mass by filtration and extraction techniques.

The preparation of the halide, such as the bromide employed in the above reaction, can be obtained by known processes starting from, in the case of the bromoanthracene derivative, anthrone.

To facilitate understanding the preparation of the starting material, reference will be made to the manner in which 9-propylbromoanthracene is prepared. In particular, anthrone is converted into 3-(9-anthracenyl)-propionic acid. Such is obtained by reacting the potassium enolate salt of anthrone with acrylonitrile in t-butyl alcohol using potassium t-butoxide as the condensing agent. The product is hydrolyzed with aqueous HCl and reduced with zinc dust in ammonium hydroxide to produce the $\beta$-(9-anthranyl)propionic acid according to the method disclosed by Daub, et al., *Journal of the American Chemical Society*, 74, page 4449 (1952). The crude product is obtained in about 90% yield, but drops to about a 52% yield following recrystallization from acetic acid.

The acid derivative, 3-(9-anthracenyl)-propionic acid, is reduced to the alcohol employing $LiAlH_4$ according to the procedure disclosed by Amitai, et al., *Biochemistry*, 21, page 2060 (1982). The alcohol is then converted to the bromide by reacting with carbontetrabromide in the presence of triphenyl phosphine according to the procedure disclosed by Duncan, et al., *Journal of Labelled Compounds*, Radiopharm, XIII, page 275 (1976).

Compounds, in accordance with the present invention, wherein $R_1$ is a hydroxyl derivative can be prepared by reacting a compound of the formula $ArR_4$ wherein Ar is the same as defined above and $R_4$ is a glycidyl ether group; with a compound of the formula $R_2SR_3$ wherein $R_2$ and $R_3$ are the same as defined above in the presence of hydrogen ions and non-nucleophilic anions such as those from the group of $SbF_6$, $PF_6$, $AsF_6$, $BF_4$, $CF_3SO_3$, and $ClO_4$. The reaction is carried out in an organic diluent. The hydrogen ions and counter ions can be provided by employing an acid of the counter ion such as $HSbF_6$, $HPF_6$, $HAsF_6$, $HBF_4$, $CF_3SO_3H$, or $HClO_4$, or employing a mineral acid such as HCl or $H_2SO_4$ along with a sodium, lithium, or potassium salt of the counter ion such as $KSbF_6$, $KPF_6$, $KAsF_6$, $KBF_4$, $CF_3SO_3M$, and $KClO_4$.

The purpose of the hydrogen ion is to open the epoxy ring to facilitate the attack by the sulfide employed. Use of the acid form of the counter ion is preferred since the presence of the mineral acids with a strongly nucleophilic anion will tend to slow the reaction somewhat.

Typical diluents employed are those in which the sulfide and glycidyl ether compounds are miscible and include acetonitrile. It is desirable that the diluent be relatively volatile in order to facilitate evaporation in subsequent process steps.

With respect to preparation of the glycidyl ether, reference will be made to the preparation of anthracenyl glycidyl ether to facilitate understanding of the present invention, it being recognized that other starting materials to provide the desired glycidyl ether can be employed utilizing the same general reaction.

In particular, anthrone is reacted with epichlorohydrin in an organic diluent such as absolute ethanol. The ethanol may be replaced by any anhydrous solvent that is miscible with water, such as anhydrous methanol or isopropanol.

Also, the epichlorohydrin, which is the source of the epoxy functionality, can be replaced by other reactive epoxies if a greater alkyl group is desired. The epichlorohydrin or epoxy compound is employed in great excess of the stoichiometric amounts, such as about 5 times to about 10 times the stoichiometric amounts. The reaction is carried out in the presence of a hydroxide such as sodium hydroxide, potassium hydroxide, or ammonium hydroxide in amounts slightly in excess of equimolar amounts of anthrone. The reaction is carried out at temperatures from normal room temperatures to about 70° C. with the preferred temperatures being about 65° C. to about 70° C. The reaction is usually carried out for about 12 hours to about 72 hours, a typical time being about 24 hours at about normal room temperature. The desired glycidyl ether can then be separated from the reaction mass by dissolving in a solvent such as chloroform or other chlorinated solvents that exhibit negligible solubility in water. Removal of the solvents used in the reaction and any other volatiles followed by crystallization from a hydrocarbon such as hexane, pentane, xylene, or toluene are used to provide the glycidyl ether product. In addition, the product can be recrystallized from methylene chloride/hexane to increase the purity of the desired glycidyl ether product.

The following non-limiting examples are presented to further illustrate the present invention.

EXAMPLE 1

Preparation of 3-(9-anthracenyl)-propyl diphenyl sulfonium hexafluoroantimonate.

About 200 ml of t-butyl alcohol are added to a 1-liter 3-neck flask with ground glass joints fitted with a dropping funnel, condenser, and mercury sealed stirrer under nitrogen atmosphere. About 4.88 grams of potassium are dissolved in the alcohol and about 19.4 grams of anthrone are added in the presence of about 10 ml of t-butyl alcohol. The solution is stirred for about 1 hour at about normal room temperature, resulting in potassium anthranilate.

To the solution of the potassium anthranilate is added, dropwise over about 1 hour, a solution of about 7.3 ml of acrylonitrile in about 40 ml of anhydrous t-butyl alcohol. During the addition of the acrylonitrile, a bright red precipitate separates out of the solution. The solution is refluxed for about 2 hours and a clear red colored solution is obtained. About 11 ml of concentrated hydrochloric acid in about 225 ml of water is added, afterwhich the t-butyl alcohol is removed by distillation. During this time, an additional 100 ml of water is added. After removal of about 350 ml of distillate, the contents remaining in the flask are cooled and the aqueous layer is separated from a brown oil by decantation. The oily nitrile is then refluxed for about 2 hours with about 100 ml of concentrated hydrochloric acid, during which time a solid acid is separated. After cooling, the hydrochloric acid is removed with the aid of a sintered glass filter stick and the remaining solid in the flask is washed with about 100 ml of water.

The acid is dissolved in about 360 ml of concentrated ammonium hydroxide and about 240 ml of water. The resulting solution is heated at about 90°–95° C. in an oil-bath for about 4 hours with about 60 grams of zinc dust activated with copper sulfate. The reaction mixture is then cooled and filtered to remove any excess zinc and the filtrate is then extracted with ether.

The aqueous layer is acidified with hydrochloric acid and a tannish oil is separated that solidifies on standing. The solid is filtered, washed with water, and then dried to give about 22.5 grams or about 90% yield of β-(9-anthranyl)-propionic acid having a melting point of about 190°–193° C. and being pale yellow crystals. The product is then recrystallized from glacial acetic acid to thereby give a pale yellow prism-like product having a melting point of about 194°–195° C. and a yield of about 52%.

About 15 grams of the 3-(9-anthracenyl)-propionic acid in dry tetrahydrofuran is added over a 2 hour period to a stirred suspension of about 5 grams of LiAlH$_4$ in about 40 ml of dry tetrahydrofuran. After stirring overnight, the mixture is placed in an ice-bath and about 10 ml of ethyl acetate is slowly added, followed by about 75 ml of ice cold water and then about 20 ml of a 20% aqueous solution of HCl. After stirring for about 2 hours, the mixture is then extracted with ether and the organic phase is washed with saturated NaCl. It is then dried over magnesium sulfate and concentrated to yield a crude product. The crude product is then recrystallized from ether/hexane to yield the purified alcohol in about a 71% yield.

About 12.7 grams of 3-(9-anthracenyl)-propionic alcohol is mixed with about 19 grams of triphenyl phosphine in about 30 ml of tetrahydrofuran and about 100 ml of diethylether. To this mixture is added about 18 grams of carbon tetrabromide (CBr$_4$). The resultant mixture is then stirred for about 60 hours. The 9-(3-bromopropyl) anthracene is then obtained by evaporation of the solvent, followed by elution on silica gel.

A slurry of about 2.234 grams (0.0037 mole) of silver hexafluoroantimonate dioxane adduct (AgSbF$_6$·3C$_4$H$_8$O$_2$), about 0.62 ml (0.0037 mole) of diphenyl sulfide, and about 2 ml of dichloromethane are added to a 3-neck, 25 ml flask through which nitrogen is bubbled before and slowly during the subsequent additions. To this stirred slurry is added a solution of about 1 gram (0.0033 mole) of the 9-propylbromoanthracene obtained above in about 5 ml of dichloromethane over about a 5 minute period. The reaction mixture is then stoppered and stirred at about room temperature and protected from light for about 10 days.

The dark colored mixture is then transferred to an Erlenmeyer flask using warm dichloromethane to provide a total volume of about 75 ml. Decoloring carbon and Celite are added (about 0.1 gram of each) and the contents are heated to boiling and filtered twice to remove the remaining traces of carbon.

The filtrate is then evaporated to dryness to give about 2.49 grams of a dark colored residue which is extracted about 3 times, 50 ml each time, with hot hexane. The hexane extract yielded about 0.284 grams of a mobile yellow oil which, according to NMR, indicates that there is about an equal molar mixture of 9-propylbromoanthracene and diphenyl sulfide that corresponds to about 18% unreacted starting materials.

The resultant dark colored solid of about 2.15 grams is dissolved in about 45 ml of warm dichloromethane, and about 40 ml of ether are added to the filtrate. The filtrate is permitted to stand at room temperature, followed by refrigeration which then provided about 1.17 grams of gold black crystals having a decomposition temperature of about 201°–203° C. The product can then be further recrystallized giving gold colored crystals having a decomposition temperature of about 202°–204° C. The product obtained is the desired [3-(9-anthracenyl)propyl]diphenylsulfonium hexafluoroantimonate as determined by NMR and IR.

EXAMPLE 2

A composition containing about 78% by weight of epoxide polymer, available from Celanese under the trade designation SU-8; about 5% of an epoxy, available from Dow under the designation XD7342; and about 17% by weight of cycloaliphatic epoxy, available from CibaGeigy under the designation CY-179 is provided. To this epoxy composition is added about 5% by weight based upon the above epoxy solids of the [3-(9-anthracenyl)propyl]-diphenyl sulfonium hexafluoroantimonate. XD7342 can be represented by the formula:

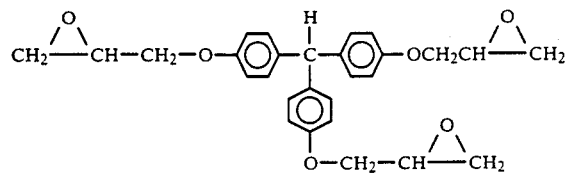

CY-179 is represented by the formula:

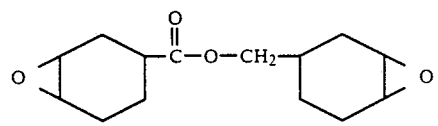

The composition is exposed to about 450 millijoules/cm$^2$ with a subsequent 100° C.-10 minute bake using a Stauffer 21-step wedge test. The above composition exhibited a 15-step hold.

COMPARISON EXAMPLE 3

Example 2 is repeated, except that the [3-(9-anthracenyl)-propyl] diphenyl sulfonium hexafluoroantimonate is replaced by a 50/50 mixture of the following compounds:

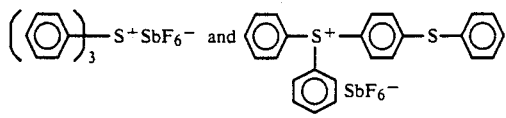

and

The results of the Stauffer 21-wedge step illustrate that the use of the above compound only holds at the 2-step.

A comparison of Example 3 with Example 2 illustrates the significant improvement achieved by the present invention and, in fact, illustrates about a greater than 10-fold increase in the photospeed.

In addition, the compound employed in Example 2 exhibits absorption characteristics of the anthracene moiety with maxima at 349 nanometers, 367 nanometers, and 387 nanometers, values at 365 nanometers and 405 nanometers are about $1.1 \times 10^4$ $M^{-1}{}_{cm}{}^{-1}$ and 110 $M^{-1}{}_{cm}{}^{-1}$, respectively.

In contrast, the sulfonium salt photoinitiators commercially available, such as those illustrated in Comparison Example 3, possess values well below 100 $M^{-1}{}_{cm}{}^{-1}$ at 365 nanometers.

A major emission line from the mercury arc lamp is centered at about 365 nanometers.

EXAMPLE 4

Preparation of 3-(9-anthracenyl)-2-hydroxy-3-oxypropyl diphenyl sulfonium hexafluoroantimonate About 9.7 grams (0.05 mole) of anthrone is placed in a 100 ml round-bottom 3-neck flask equipped with a dropping funnel, nitrogen purge, magnetic stirrer, and condenser. About 23 grams (0.25 mole) of epichlorohydrin in about 8 ml of absolute alcohol are added to the reaction flask and the contents are warmed to about 65° C. During this time, most of the anthrone is dissolved.

About 2.6 grams (0.065 mole) of sodium hydroxide are dissolved in about 3 ml of water and then added to the reaction flask, dropwise over about 2 hours. The temperature of the reaction mass during this time is maintained at about 65°–75° C. The reaction mass is then allowed to slowly cool and is stirred for about 20 hours at normal room temperature. Upon the cooling, a precipitate is formed. About 50 ml of chloroform is added to dissolve the precipitate, most of which is dissolved leaving an oily, white solid of about 3.6 grams which is washed with chloroform and filtered off.

The reaction solvents and other volatiles are then removed by heating at about 50°–60° C., leaving about 14 grams of an oily, orange solid remaining.

The above crude product is then crystallized from hexane, whereby about 2 grams of a dark orange oil that is insoluble in hot hexane are discarded. About 6.3 grams of recrystallized product having a melting point of about 96°–100° C. are obtained. An additional 2.1 grams of a further recrystallized product having a melting point of about 88°–95° C. are obtained.

These products are then recrystallized from methylene chloride-hexane to yield about 4.9 grams of a first product having a melting point of about 96°–100° C. and a second product of about 1.7 grams having a melting point of about 95°–100° C.

The supernatants of the above recrystallizations give about 2.6 grams of material having a melting point of about 81°–89° C. and recrystallization from the hexane resulted in about 2 grams having a melting point of about 85°–95° C.

The overall yield corresponds to about 70%. The obtaining of the desired 9-anthracenyl glycidyl ether is confirmed by NMR and IR spectra.

About 0.9 grams (about 2.6 m mole) of hexafluoroantimonic acid are added to a 50 ml round-bottom flask equipped with magnetic stirrer.

A solution of about 1 gram (4 m mole) of the 9-anthracenyl glycidyl ether obtained above, about 2 grams (11 m mole) of diphenyl sulfide, and about 2 grams of acetonitrile is provided. About half of this solution is added to the reaction flask over about 30 minutes, followed, in turn, by the addition of another 0.9 grams of the hexafluoroantimonic acid. The remaining half of the glycidyl ether solution is then added.

The reaction is allowed to proceed for about 40 minutes after the addition of the glycidyl ether solution, followed by evaporation of the acetonitrile.

The resulting oil product is then taken up into dichloromethane. The mass is then dried with magnesium sulfate and filtered. The solvent is concentrated to about 4 mL and ether is added to yield an oily solid of about 0.7 grams that represent about a 26% yield. This product is then crystallized from 1,2-dichloroethane to give yellow crystals of about 3.5 grams having a melting point of about 172°–175° C.

The desired product is confirmed by the NMR spectrum.

EXAMPLE 5

Example 2 is repeated, except that the compound of Example 4 is employed in place of the [3-(9-anthracenyl)-propyl] diphenyl sulfonium hexafluoroantimonate. The results of the Stauffer 21-step wedge test illustrate that 12 steps are held employing the compound of this example.

COMPARISON EXAMPLE 6

Preparation of 3-(9-anthracenyl)-2-hydroxy-3-oxypropyl dimethyl sulfonium hexafluoroantimonate About 1 gram (2.9 m mole) of hexafluoroantimonic acid and about 1.5 grams (24 m mole) of dimethyl sulfide are placed in a 100 ml round-bottom flask. A solution of 9-anthracenyl glycidyl ether of 2 grams (8 m mole) prepared according to the procedure of Example 4 in about 5 grams (81 m mole) of methyl sulfide is prepared. About 2 grams of the solution are added dropwise to the reaction flask, afterwhich about 1 gram of additional hexafluoroantimonic acid is added, then another 2 grams of the glycidyl ether solution, followed by an additional gram of the hexafluoroantimonic acid, followed by another gram of the glycidyl ether solution. The reaction mass is stirred for about 30 minutes at about room temperature. About 3 ml of water and about 10 ml of acetonitrile are added and the reaction is stirred for about 10 minutes. The volatiles are removed by rotoevaporation, leaving an oil and an aqueous layer. The oil layer is extracted into dichloromethane. A portion of the oil is insoluble, which insoluble portion is taken up into acetone after decanting off the aqueous layer. Both the dichloromethane and acetone layers are dried over magnesium sulfate, filtered, treated with charcoal and Celite, filtered and rotoevaporated to leave an oil. Upon evaporation of the dichloromethane, about 2.5 grams of an orange oil is obtained which is then redissolved in dichloromethane and treated with charcoal. The solution is then placed in a freezer and about 1.5 grams of crystals having a melting point of about 109°–119° C. are obtained. The crystals are then washed with dichloromethane to yield about 1.25 grams having a melting point of about 115°–122° C. A second crop of crystals of about 0.2 grams are obtained.

Evaporation of the acetone solution resulted in about 1.3 grams of a dark colored oil which then was taken up in the dichloromethane. Approximately ½ of the oil dissolved, leaving behind a dark-colored oil of about 0.6 grams. The solution is treated with charcoal, filtered, and then reduced in volume.

Hexane is added until cloudiness appeared and crystals formed on standing about 0.2 grams having a melting point of about 116°–120° C. and a second crop of crystals of about 0.2 grams having a melting point of about 105°–116° C.

The crude yield is about 3.8 grams, which is about 85% yield with a first crop crystals amounting to about 1.25 grams or about a 28% yield and a total yield of crystals of about 2.1 grams of about 48% yield. The product is 3-(9-anthracenyl)-2-hydroxy-3-oxypropyl dimethyl sulfonium hexafluoroantimonate as confirmed by NMR spectra.

The above compound is employed in the epoxy compositions disclosed in Example 2. The above compound did not exhibit any photoinitiating activity.

This example illustrates that compounds which differ from those of the present invention in having both $R_2$ and $R_3$ being alkyl do not possess the activity of the compounds of the present invention.

Having thus described our invention, what we claim as new and desire to secure by Letters Patent is:

1. A compound having the formula:

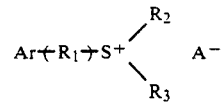

wherein Ar is a fused aromatic radical selected from the group of anthracyl, peryl, and pyryl; $R_1$ is a divalent bridge selected from the group of alkylene and alkenylene, alkylene and alkenylene chains broken with an oxygen atom; and substituted derivatives thereof having a hydroxyl group pendant from the chain; each $R_2$ and $R_3$, individually, is selected from the group of alkyl, aryl, alkaryl, aralkyl, and substituted aryl, provided that not more than one of $R_2$ and $R_3$ is alkyl; and $A^-$ is a non-nucleophilic anion.

2. The compound of claim 1 wherein Ar is anthracyl.

3. The compound of claim 1 wherein $R_1$ contains 1–10 carbon atoms.

4. The compound of claim 1 wherein $R_1$ contains 1–4 carbon atoms.

5. The compound of claim 1 wherein $R_1$ contains 3 carbon atoms.

6. The compound of claim 1 wherein $R_1$ contains a pendant hydroxy group.

7. The compound of claim 1 wherein $A^-$ is a non-nucleophilic anion selected from the group of $SbF_6$, $PF_6$, $AsF_6$, $BF_4$, $CF_3SO_3$, and $ClO_4$.

8. The compound of claim 1 wherein $A^-$ is $SbF_6$.

9. The compound of claim 1 wherein each $R_2$ and $R_3$ is phenyl.

10. The compound of claim 1 wherein each $R_2$ and $R_3$ is phenyl or an alkyl group of 1–4 carbon atoms provided that not more than one of $R_2$ and $R_3$ is alkyl.

11. The compound of claim 1 which is 3-(9-anthracenyl, propyl diphenyl sulfonium hexafluoroantimonate.

12. The compound of claim 1 being 3-(9-anthracenyl)-2- hydroxy-3-oxypropyl diphenyl sulfonium hexafluoroantimonate.

* * * * *